United States Patent [19]

Ryder et al.

[11] 4,178,932
[45] Dec. 18, 1979

[54] VACUUM CURETTAGE DEVICE WITH VACUUM INDICATOR

[75] Inventors: Francis E. Ryder, Barrington, Ill.; Michael D. Thomas, Arab, Ala.

[73] Assignee: Ryder International Corporation, Barrington, Ill.

[21] Appl. No.: 830,770

[22] Filed: Sep. 6, 1977

[51] Int. Cl.² .............................................. A61M 1/00
[52] U.S. Cl. .................................... 128/276; 116/272
[58] Field of Search ............... 128/276, 297, 2 F, 245; 15/337; 116/114 PV, 114 AP, 117 R; 137/551; 55/21, 34, 274; 99/472

[56] References Cited

U.S. PATENT DOCUMENTS

| | | | |
|---|---|---|---|
| 2,445,176 | 7/1948 | Hoffman | 116/114 PV |
| 3,334,628 | 8/1967 | Saemann et al. | 128/276 |
| 3,738,311 | 6/1973 | Appleton | 116/114 PV |

FOREIGN PATENT DOCUMENTS 882165  11/1961  United Kingdom ...................... 55/274

*Primary Examiner*—Robert W. Michell
*Assistant Examiner*—J. L. Kruter
*Attorney, Agent, or Firm*—Trexler, Wolters, Bushnell & Fosse, Ltd.

[57] ABSTRACT

There is disclosed a device for performing medical procedures such as curettage, or the like, employing the use of an evacuated vessel, a cannula or similar form of medical implement and a valve arrangement for selectively applying the vacuum to the cannula. An improved vacuum indicator is included within the vessel for providing a positive visual indication as to the presence or absence of an acceptable vacuum level therein. In addition the disclosed embodiment includes a vial or the like for the collection of tissue samples within the vessel, a cover structure for the vessel including a shoulder for engaging the inner periphery of the vial and one or more resilient fingers in concentric arrangement with the shoulder for positively engaging a complementary flange or shoulder formed about the outer periphery of the vial. One or more slots or openings are formed in the shoulder of the manifold for applying the vacuum in the vessel to the vial, and from there to the cannula via an opening in said cover structure.

11 Claims, 7 Drawing Figures

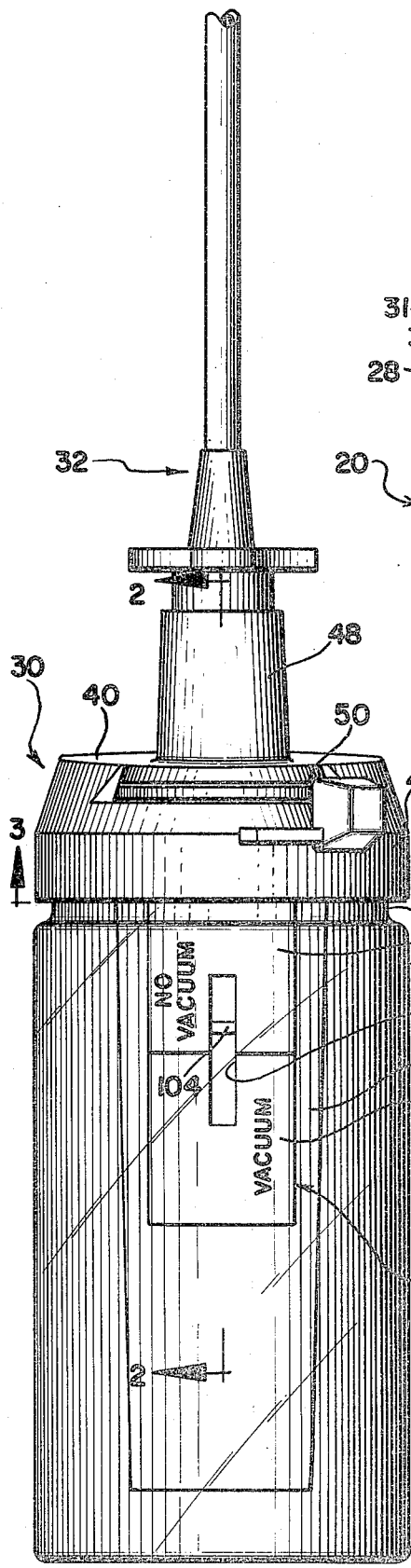
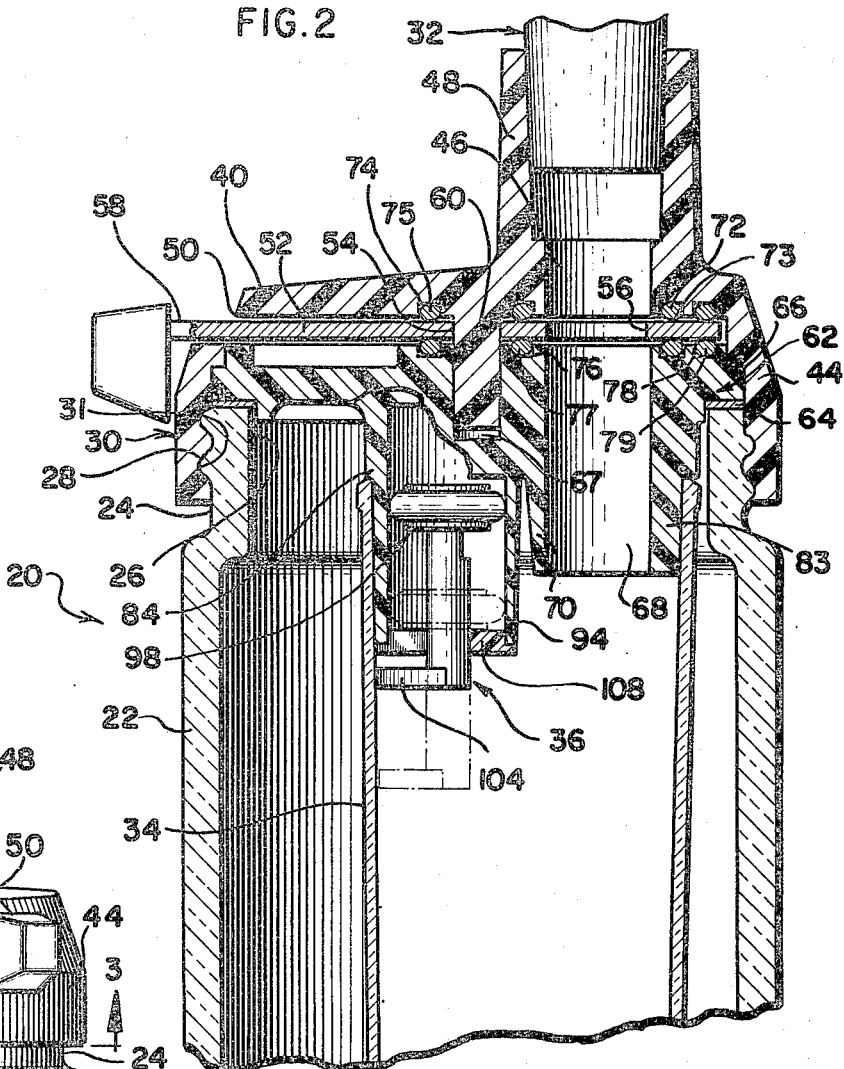
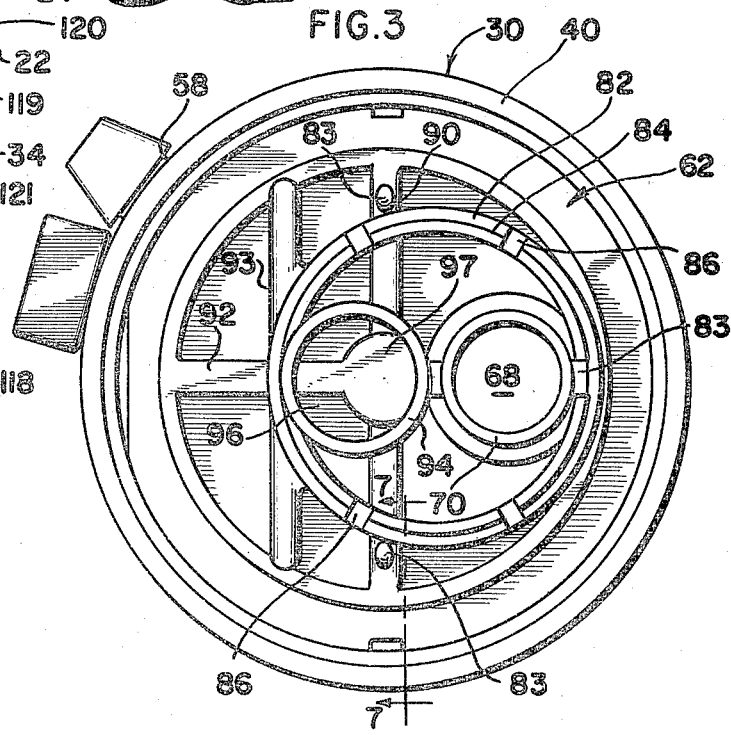
FIG.1
FIG.2
FIG.3

VACUUM CURETTAGE DEVICE WITH VACUUM INDICATOR

BACKGROUND OF THE INVENTION

This invention relates generally to an evacuated medical device and more particularly to an improved vacuum indication for devices utilizing an evacuated vessel for the performance of a curettage or some other type of medical procedure.

The present invention relates generally to and is disclosed in conjunction with an improved device as illustrated in Applicant's prior application, Ser. No. 676,759 filed Apr. 14, 1976, now U.S. Pat. No. 4,063,556. For purposes of completeness, the disclosure of said prior application is incorporated herein by reference.

By way of background, it will be noted that evacuated medical devices for performing curettage and other medical procedures are known. The prior art devices, like the device of said prior application, and as illustrated herein, generally include an evacuated vessel to which is attached a medical implement, such as a cannula, with some form of valve means being employed to apply a vacuum to said implement. These prior art devices, however, to the extent the inventors are aware, and with the exception of the embodiments in the above-cited application, do not utilize means for indicating whether a sufficient vacuum is present within the vessel.

With specific reference to the above-cited application, it will be noted that the indicator means thereof generally comprise an elastomeric member, such as a tube or bellows in which a residual quantity of air at atmospheric pressure is contained. The elastomeric member must expand upon the evacuation of the vessel to give an indication of the vacuum level. However, if the elastomeric member should leak, due to pin holes or the like being formed therein the residual quantity of air will seep into the vessel tending to produce an equilibrium condition, with the elastomeric members retracting to their original shape. This return to the original shape, would most likely be construed as an indication that the vacuum in the vessel had been lost, when in fact it had not. As such, fully usable, evacuated units have been discarded due to this erroneous indication. The present invention, however, contemplates an improved, reliable indicator member not subject to any residual elastomeric forces which might give rise to a false reading.

In addition to not being subject to the above-noted disadvantages, the device of the present invention is also possessed of other advantages and features which will become more readily apparent upon a consideration of the following descriptions in conjunction with the attached drawings and detailed discussion of the illustrated embodiment. More specifically, the vacuum indicator of the present invention employs a closed bottom cylinder in which is disposed a piston member. The piston member, includes sealing means in slidable contact with the cylinder's interior wall. The closed bottom of the cylinder includes a recessed portion such that upon disposition of the piston member in the cylinder a residual quantity of air will remain trapped. In addition the present invention contemplates means for maintaining the co-axial orientation of the piston member, and also means to preclude ejection of the piston from the cylinder when the vessel is evacuated. As will become apparent, the quantity of residual air trapped, determines the sensitivity of the indicator and the length of the stroke of the piston upon evacuation of the vessel. Accordingly, upon evacuation of the vessel, due to the residual air at atmospheric pressure a pressure differential will be created across the piston, causing it to move axial of the cylinder. As the piston moves, the quantity of residual air is expanded and its pressure drops. The pistion, theoretically and given a chamber of sufficient length will continue to move until a state of equilibrium is reached, i.e. wherein the pressure differential is no longer sufficient to overcome the sliding frictional forces produced by engagement of the piston with the cylinder side walls. In the present invention means are provided for terminating movement, at a point determined, taking into account the quantity of residual air, as sufficient for indicating an acceptable vacuum level.

With regard to the above discussion concerning the prior devices, and their problems, it should be noted that with the arrangement discussed above, and to be described in greater detail hereinafter does not rely upon exposure of an elastomeric member to obtain an indication of a vacuum. As such, the problem of false indication of loss of vacuum will not occur. More specifically, assuming an evacuated vessel and movement of the indicator to a given location, should the O-ring seal leak but the cover seal remain effective, the pressure differential across the piston might be lost, but it never will be reversed such as would cause the piston to move upwardly toward the closed end. On the other hand, if the cover seal leaks, the vacuum in the vessel will be lost and as air enters the vessel the ambient pressure will rise. Soon a level will be reached which is greater than the pressure on the closed side of the piston (keeping in mind that this pressure is less than atmospheric due to expansion of the residual quantity of air pursuant to initial movement). Accordingly, a pressure differential will be created causing the piston to move upwardly to a position wherein a visual indication is provided to the effect that the vacuum has become lost. The only possible instance wherein the device can provide a false reading is, if the O-ring seal fails and then subsequently the cover seal fails. Should this rather unlikely sequence of events occur, the indicator would register an acceptable level of vacuum when in fact none exists.

A preferred form of the present invention will be discussed and is illustrated in the drawings, and it should be kept in mind that said discussion and illustration are not intended to define the limits of the invention. To the contrary, it is contemplated that those skilled in the art and possessed of the present disclosure, may devise various alternate structures, constructions or modifications, which fall within the spirit and scope of this invention as defined by the claims appended hereto.

BRIEF DESCRIPTION OF THE DRAWINGS

In the drawings, in which like reference numerals are used throughout to designate like elements and components:

FIG. 1 is an elevational view of a medical device constructed in accordance with the present invention;

FIG. 2 is a somewhat enlarged partial sectional view, taken generally along the line 2—2 of FIG. 1;

FIG. 3 is a horizontal sectional view taken generally along the line 3—3 of FIG. 1;

DETAILED DESCRIPTION OF THE ILLUSTRATED EMBODIMENT

Figure 4:
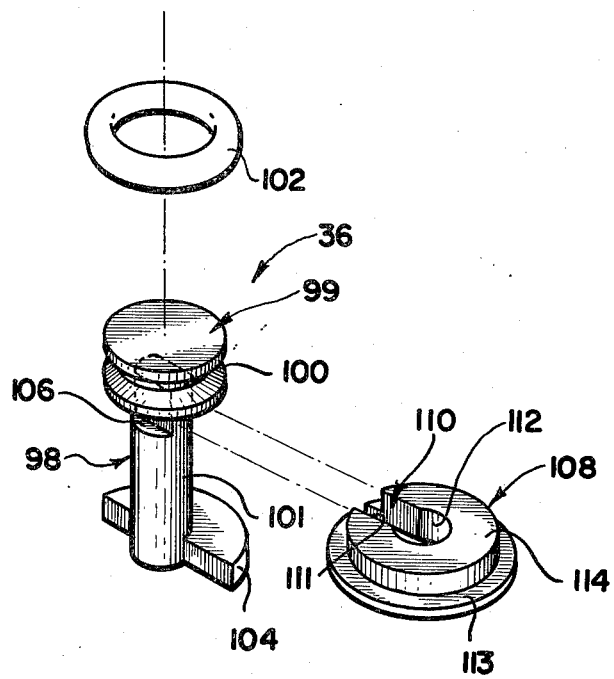
FIG. 4 is an exploded perspective view, revealing additional detail of selected elements of the indicator of the present invention.

Referring initially to FIGS. 1 and 2, a medical device 20 is illustrated, constructed in accordance with the present invention, and suitable for use in a curettage procedure. FIG. 1 illustrates the device 20 in fully assembled condition, while FIG. 2 is a somewhat enlarged and partially cut away section taken generally along the line 2—2 of FIG. 1.

The medical device 20 is similar to that as described in detail in U.S. patent application Ser. No. 676,759, and includes a vessel 22 adapted to be evacuated thereof. The vessel 22 includes a neck portion 24 which terminates in an opening 26, said neck portion 24 including an external thread 28 to which a complementary threaded portion 31 of a combination cover and valve assembly 30 is connected. A medical implement 32, such as a cannula for performing curettage procedures is connected to the combination cover and valve assembly 30. Thus, upon evacuation of the vessel 22, the vacuum therein can be applied selectively to the cannula 32 through the operation of a valve mechanism, to be described more fully hereinbelow.

Note will be taken at this point that the medical device 20 also includes a vial 34 for the collection of tissue specimens, and indicator means, designated generally 36 within the vessel which is adapted to provide a visual indication as to the presence or absence of vacuum therein. These elements will be described more fully hereinbelow.

The combination cover and valve assembly 30 includes a cover member 40 having an annular downwardly depending rim 44 wherein the thread 31 is internally formed for engagement with the thread 28 on the neck 24 of the vessel 22. The cover member 40 also includes an opening or aperture 46 extending therethrough, and on the upper surface thereof, a relatively short tubular section 48, in alignment with the opening or aperture 46, which is adapted to receive the end of the cannula 32. The cover member 40 also includes an arcuate through slot 50 proximate the rim 44 and at one side thereof for receiving a tab or actuator element of the valve plate.

The valve mechanism includes a valve plate 52 having a central aperture 54 and a somewhat larger, radially offset aperture 56. The plate 52 includes a peripheral tab 58 which extends through the slot 50 upon assembly. The valve plate 52 is mounted interiorly of the cover 40, with the central aperture 54 being rotatably engaged over a downwardly depending post 60 formed on the inner surface of the cover 40. Thus, the disposition of the aperture 56 relative to the aperture or opening 46 of the cover section 40 can be controlled through the manipulation of the tab 58.

A manifold member 62 is also disposed within the cover member 40, being generally of a shape conforming to the shape of the portion thereof radially interior the downwardly depending rim 44 thereof, and of sufficient size to overlie the rim of the vessel neck 24 with a gasket 64 being provided therebetween to effect an airtight seal. The manifold member 62 is generally received within the cover member 40 and engaged against an abutment shoulder 66 formed interiorly of the rim portion 44 thereof, and includes a central recess 67 in which is engaged the end of the post 60 with a force fit to attain assembly of the manifold member 62 within the cover member 40. With the manifold member 62 assembled as shown in FIG. 2, the valve plate 52 is clamped between the manifold member 62 and cover member 40, the seating of the manifold 62 on the shoulder 66 preventing over-clamping of the valve plate 52 whereby said valve plate remains freely rotatable. The manifold member 62 further includes a through aperture 68 which is defined partially by a tubular section 70 thereof extending downwardly from the lower surface portion thereof into the vessel 22. Assembly of the manifold member 62 with the cover member 40 is effected so that the aperture 68 is in alignment with the aperture or opening 46 in the cover member 40.

As can be seen in FIG. 2, communication between the apertures or openings 68 and 46 is controlled by the rotation of the valve plate member 52 and relative disposition of the aperture 56 therein with respect to the apertures or openings 68 and 46. Thus, manual actuation of the tab 58 may be employed to alter the relative position of the aperture 56 in order to achieve interconnection of the respective apertures or openings 68 and 46, thus effecting the application of vacuum within vessel 22 to the cannula 32.

As can be appreciated, a sealing arrangement for the valve mechanism must be provided, and this arrangement can best be understood with reference to the aforementioned prior application. Essentially, said seal arrangement includes a pair of channels 72 and 74 in the cover portion 40 in which are disposed a pair of O-ring seals 73 and 75, which engage the upper surface of the valve plate member 52. Correspondingly, a pair of grooves 76 and 78 are provided in the upper surface of the manifold member 62, having a similar pair of O-ring seals 77 and 79 disposed therein, and in engagement with the undersurface of the valve plate 52. It will be noted, that the channels 72 and 76 circumscribe the apertures or openings 46 and 68, respectively. Thus, the O-ring seals 73 and 77 therein provide an airtight seal with the valve plate 52 therebetween, and more particularly, a seal is formed thereby between the apertures 46 and 68 and the aperture 56, when said apertures are in alignment. The grooves 74 and 78 are aligned eccentrically, whereby the O-rings 75 and 79 therein provide an airtight seal with the valve plate 52, the aperture 56 thereof being enclosed within the seal, regardless of the position thereof as the plate 52 is rotated by actuation of the tab 58. Again, this arrangement which forms no essential part of the present invention is disclosed in detail in said prior application.

The foregoing parts, and the arrangement, interconnection and functions thereof, are substantially similar to that described for similar parts in the co-pending application Ser. No. 676,759, cited above and incorporated by reference herein. Therefore, further discussion of these parts is deemed unnecessary herein.

Figure 7:
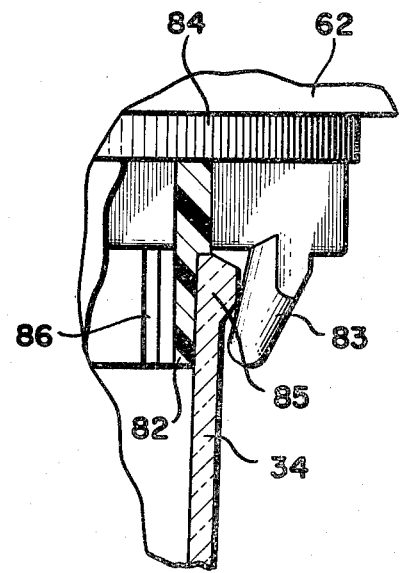
FIG. 7 is an enlarged view, partially cut away, taken generally along the line 7—7 of FIG. 3.

Attention is now directed to the improved means provided for mounting the vial 34 to the manifold member 62, with particular reference to FIGS. 2, 3 and 7.

It will be noted that the manifold member 62 also includes an annular, downwardly depending flange 82 disposed outwardly of and generally eccentrically with respect to a tubular segment 70, such that an outwardly extending spacer portion 83 of the tubular segment 70 forms a minor fractional part of the flange 82. The flange 82 is stepped to provide an abutment shoulder 84 and also includes a series of slots 86 formed therein which slots extend to a location disposed above said abutment shoulder 84 and in effect divide the flange into a number of flexible segments, such that said flange 82 may be termed resilient. The opening of the specimen vial 34 is of such dimension that when the vial is engaged over the flange 82, the aforementioned segments of said flange will be flexed inwardly to provide a friction fit with the vial. Additionally, the manifold member 62 is provided with a pair of downwardly extending finger members 83 outboard of the flange 82 and spaced apart therefrom by substantially the radial width of the abutment shoulder 84 thereof. It will be noted that the vial 34 is provided with an outwardly extending flange or shoulder portion 85 surrounding the opening thereof, whereby the fingers 83, being somewhat resilient, flex somewhat to first receive and then positively engage the flange or shoulder 85 of the vial 34, thus insuring a suitable connection or fit between the vial 34 and the manifold 62. Thus, the vial 34 is securely engaged with the manifold 62 by moving the vial axially of the flange 82 until the upper edge thereof is engaged with the abutment shoulder 84 and the flange portion 85 thereof is engaged by the fingers 83.

Since the slots 86 extend upwardly beyond the shoulder 84, the upper portion of the slots 86 remain open and uncovered by the vial 34. These open, upper portions of the slots 86 provide a path for the vacuum from the vessel 22 interiorly of the vial 34. As can be appreciated, since a path is provided for a vacuum interiorly of the vial 34, said vacuum can be applied to the aperture 68 and from there to the cannula 32. Preferably, the slots 86 formed on the flange 82 are disposed remote from the tubular section 70. In consequence of the downward extent of the tubular section 70 within the vial 34, the relatively higher position of the open portions of the slots 86, and the disposition of said slots remote from the tubular section 70, the vacuum from the vessel 22 is applied to the vial 34 by a substantially circuitous route. Thus, as tissue specimens enter the vial 34, they will tend to fall to the bottom thereof, rather than being drawn into the slots 86. It will further be noted that the underside of the manifold 62 is provided with a lattice of strengthening ribs 90, 92 and 93 which prevent flexing of the member 62 under any resultant forces produced due to the pressure differential created upon evacuation of the vessel 22. It will be noted that the downwardly extending finger members 83 are mounted upon the strengthening rib 90. Thus, the integrity of the fit between parts above described, and especially the sealing arrangement of the valve plate 52 and the fitting of the vial 34 to the manifold 62, is maintained.

Attention is now directed to the indicator means 36 of the present invention. As discussed above, it is desirable to provide the potential user with some visual indication as to whether or not a vacuum still existed within the vessel preparatory to use, without actually opening the valve. While the embodiments as disclosed in said copending application are effective in this regard, they are, as discussed above, subject to certain disadvantages. Accordingly, the present invention provides a novel and improved type of vacuum indicator, which does not rely upon the elastomeric deformation of an enclosed envelope or the like, to provide an indication of the vacuum level.

Directing attention intially to FIG. 2, it should be noted that the manifold 62 includes a downwardly extending tube or cylinder 94, located within the downwardly extending flange 82. The cylinder 94 is spaced apart somewhat from the tube 70, and has an outer wall segment thereof aligned with the flange 82 to be coextensive with a minor fractional part thereof. Moreover, the cylinder 94 extends downwardly into the vial 34, when said vial is assembled with the manifold 62, for some distance below the extent of the flange 82 and the tube 70. The cylinder 94 includes an open end 95 and closed end or bottom wall 97. As illustrated, the cylinder 94 is formed integral with the manifold 62. While this is preferred, the cylinder 94 may be formed separately as a closed bottom vessel and merely affixed to the manifold 62. With reference to FIG. 3, it will be noted that the bottom wall 97 is defined partially by support ribs 90 and 92 which provide a pair of recessed portions or chambers 96.

Disposed within cylinder 94 is a piston member, designated generally 98. The piston member 98 includes an enlarged head portion 99 having an annular groove 100 formed therein. Received in the groove 100 is an elastomeric sealing member 102 in the form of an O-ring. O-ring 102 is selected to have an inner diameter somewhat less than the diameter of groove 100. Accordingly, when assembled, the O-ring will tend to return to its original position thereby molding itself to the wall surface of groove 100 and assuring a proper seal along said wall surface. Extending from the enlarged head portion 99 is an elongate shaft 101, one end of which is connected to the piston head 99, the opposite end of said shaft 101 having an indicator member 104 formed thereon, which in a preferred embodiment comprises a half-disc shaped member. It will further be noted that the shaft 101 includes a slot or notch 106 formed therein, whereby a disc-like closure member 108 may be slidably mounted with respect to the shaft 101 by means of a key hole slot 110 formed therein. The key hole type slot 110 includes an opening 111 and a central aperture 112. The opening 111 will receive the reduced portion of the shaft 101 provided by the notch 106. Once the shaft 101 is received within the central aperture 112, the disc 108 can be moved axially of the shaft and will be retained captive thereon. As can be best seen in FIGS. 4 and 5, the closure member 108 includes a flanged portion 113 and a reduced diameter portion 114. For a purpose to be discussed more fully hereinafter, it should be noted that the portion 114 is sized to be disposed within the open end 95 of cylinder 94 with a friction fit.

Figure 5:
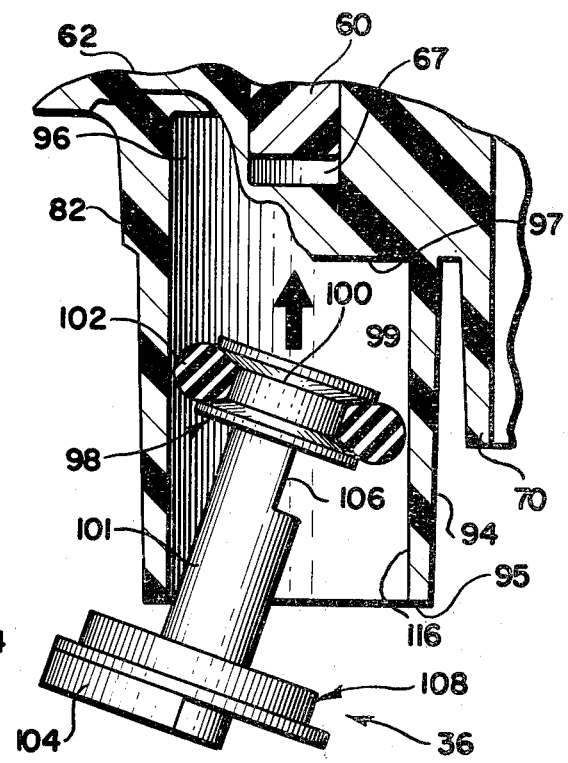
FIGS. 5 and 6 are enlarged partial sectional views illustrating a portion of FIG. 2 and the elements of the indicator of the present invention in additional detail preparatory to assembly and after assembly.
Figure 6:
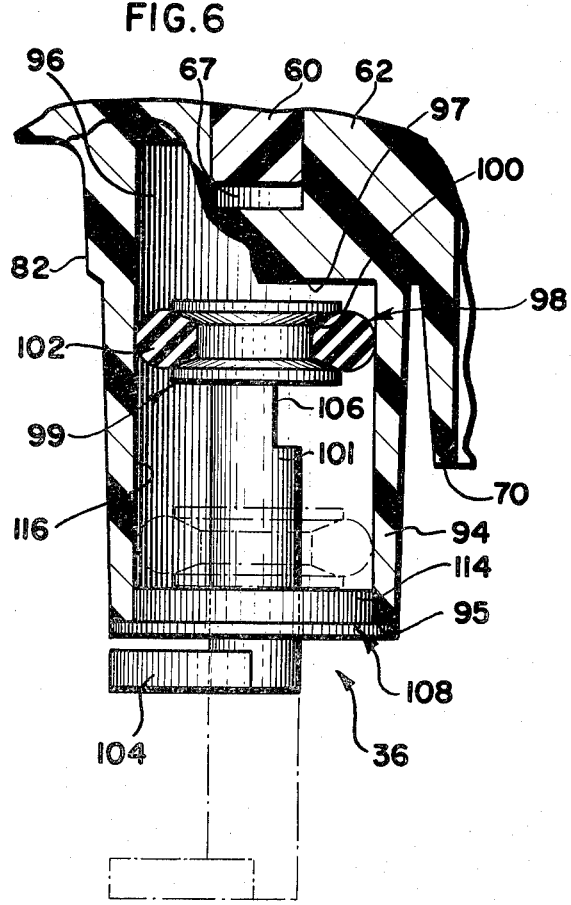

The manner of assembling or disposing the piston member 98 with respect to the cylinder 94 is illustrated in FIGS. 5 and 6. In this regard, the outer diameter of the O-ring 102 is greater than the diameter of the inner annular wall 116 of cylinder 94. If assembly of the piston 98 in cylinder 94 were attempted with the piston disposed coaxially of the inner annular wall surface 116, the O-ring 102 would be in sealing engagement; and air would be trapped behind the O-ring preventing assembly. Accordingly, assembly must be effected by tipping the piston member 98 as shown in FIG. 5. This permits the piston head 99 to move inwardly of the cylinder without the O-ring 102 engaging wall surface 116. As such, the air is spilled from behind the piston head 99. When the piston head 99 reaches the bottom wall 97 of cylinder 94, the piston member is repositioned in coaxial alignment with the cylinder 94, to bring the O-ring 102 into sealing contact with the wall surface 116, see FIG. 6. Of importance, it should be noted that a residual quantity of air will remain in the recessed portion 96 of bottom or end wall 97.

Next, the closure member 108 is assembled to the cylinder 94, by disposition of the portion 114 within the open end 95, said portion 114 engaging the wall surface 116 to provide a friction fit. Thus, recalling the fact that the shaft 101 is maintained captive with respect to the closure 108 by means of the key hole type slot 110, it can be appreciated that when assembled as shown in FIG. 6, the piston member 98 will be maintained in a coaxial relation to the cylinder 94. That is to say, the piston can only move linearly along the axis of the aperture 112 in closure 108, which is selected to coincide with the axis of the cylinder 94. Accordingly, this captive assembly of the piston 98 assures the continued sealed engagement of the O-ring 102 with the wall surface 116, and precludes tipping of the piston, such as would permit the air in the recessed portion 96 to escape.

While it is not desired to limit the operation of the indicator means 36 to any specific physical theory, the following conforms with the facts and structure thus far described and is believed to accurately and correctly describe the operation of the indicator 36, upon evacuation of the vessel 22. In this regard, the indicator means 36 is assembled as discussed above at ambient pressure, with the piston member 98 disposed proximate the end wall 97. As such, a residual supply of air substantially at atmospheric pressure is retained or trapped within the chamber 96. Thus, it will be appreciated that the piston member 98 is neutrally loaded so that its axial position within the cylinder 94 depends upon the pressure differential, if any, on either side of the O-ring seal 102. Prior to evacuation of the vessel 22 then, there being essentially atmospheric pressure on either side of the piston 98, said piston will remain in the position to which it initially was disposed in the cylinder 94, shown in solid outline in FIGS. 2 and 6. The vessel 22 can be evacuated by means of the valve arrangement previously described, preferably, the vacuum drawn is on the order of 27" of mercury. As the vacuum is drawn, a pressure differential is created across the piston 98 as the air trapped in chamber 96 is at atmospheric pressure. This pressure differential will cause the piston 98 to move axially of cylinder 94, tending to seek an equilibrium condition. This movement causes the residual air in the chamber 96 to expand and correspondingly its pressure is reduced. The piston 98 will move downward, as illustrated in dotted outline in FIGS. 2 and 6, until the piston head 99 engages the end closure 108.

Theoretically, if the closure 108 was not present, the piston 98 would move until it exits the cylinder 94, or until the residual air in chamber 96 had expanded to such an extent that its pressure in relation to the vacuum in the vessel 22 was such that the force on the piston head 99 due to the pressure differential was insufficient to overcome the frictional forces of the O-ring 102 with wall surface 116. Thus, the quantity of air trapped in the recessed portion or chamber 96 will determine the sensitivity of the indicator 36, with respect to the vacuum level drawn in vessel 22. In this regard, if a relatively small quantity of air is trapped, the movement or length of stroke of the piston will be short. Correspondingly, if a larger quantity is trapped, the stroke of piston 98 is lengthened.

In practice, the volume of the chamber or recessed portion 96 is determined empirically to provide the degree of movement desired, and practical in relation to the vessel 22. In this regard, the quantity of air is selected, such that the pressure of the residual air upon the piston head 99 reaching the closure 108 is insufficient to overcome the forces provided by O-ring 102 and the friction fit of closure 108 in the open end 95.

In order to provide a visual indication of the presence or absence of a vacuum in the vessel 22, indicia means are provided, such as a label 118, attached to or otherwise suitably formed on a side of the vial 34, as best seen in FIG. 1. In a preferred embodiment, the label 118 is opaque and includes a relatively elongate window or opening 119 formed therein, through which the indicator member 104 can be clearly observed. The label 110 and window 119 thereof preferably comprise two sections, a first or top section 120 and a lower section 121. The label is placed in relation to the indicator 36, such that when the member 104 is disposed proximate section 120 an insufficient vacuum exists within the vessel 22. Correspondingly, when member 104 is aligned with the lower portion 121, there is provided an indication of a sufficient vacuum level in the vessel 22. It will be appreciated that the chamber 96 is of suitable volume to produce the correct range of indications as described, for the degree of vacuum desired in the vessel 22.

Should the vacuum in the vessel 22 be lost or diminished during storage of the initial evacuation, the pressure differential across the piston 98 will be reduced, whereby the piston 98 and indicator 104 will tend to move upwardly in the cylinder 94, to the "no vacuum" position. Moreover, it will be noted that as the piston is essentially neutrally loaded, that a leak or the like in the O-ring 102, occurring after the evacuation of the vessel 22, will have no effect on the position of said piston and the positive indication of a vacuum in said vessel. In this regard, the effect of a leak would be merely to equalize the pressure across the piston 99, but not to create a pressure differential such as would produce upward movement. Accordingly, once the piston 99 has operated to properly indicate a vacuum upon evacuation of the vessel 22, it will not return to its original position, except in response to a loss of vacuum in vessel 22, and as such any chance of false indication of a loss of vacuum are substantially eliminated.

There has been illustrated and disclosed herein an improved evacuated medical device and vacuum indicator of a preferred design. Various changes and modifications in the disclosed structure may be apparent to those skilled in the art, and are included in the present invention insofar as they fall within the spirit and scope of the appended claims.

The invention is claimed as follows:

1. A medical device such as a curette or the like, comprising a vessel including cover structure with aperture means in the cover for attachment of a medical implement, such as a cannula, or the like, which vessel is adapted to be evacuated, valve means intermediate said vessel and said medical implement for selectively applying said vacuum to said medical implement, vacuum indicator means carried by said cover structure, interiorly of said vessel to provide a visual indication corresponding to the presence or absence of a vacuum in said vessel, said vacuum indicator means including cylinder means having a closed end and an open end, a piston member having a head portion disposed in said open end of said cylinder means, an O-ring carried by said head portion to adapt said head portion for sliding sealed engagement with the walls of said cylinder means and said piston also having a shaft of lesser diameter dimension than said head portion, and guide means with said cylinder open end receiving said shaft to maintain said head portion in co-axial alignment with said cylinder, thereby guiding the sliding sealed movement of said head portion within said cylinder means, said cylinder means including a recessed portion in said closed end and said head portion being of a lesser diameter dimension than said cylinder means to allow said head portion to enter said cylinder means in a tilted position for displacing a quantity of air from said cylinder upon assembly and for retaining a residual supply of air such that said piston member may be disposed in said cylinder means proximate the closed end thereof at atmospheric pressure to trap a quantity of air in said recessed portion, and said piston member further comprising an indicator member carried by said shaft whereby upon evacuation of said vessel a pressure differential will exist across said piston causing said retained quantity of air to expand and move said piston toward said open end, with the position of said indicator member being adapted to be employed to provide a visual indication of the existence of a vacuum in said vessel.

2. A medical device according to claim 1 further including stop means carried by said guide means proximate the open end thereof to retain said piston member member within said cylinder means.

3. A medical device such as a curette or the like, comprising a vessel including cover structure, which vessel is adapted to be evacuated, valve means for selectively applying said vacuum to a medical implement attached to said device, such as a cannula or the like, vacuum indicator means carried by said cover structure, interiorly of said vessel to provide a visual indication corresponding to the presence or absence of a vacuum in said vessel, said vacuum indicator means including cylinder means having a closed end and an open end, a piston member disposed in said open end of said cylinder means, and in sliding sealed engagement with the walls of said cylinder means, and stop means carried by said cylinder means proximate the open end thereof to retain said piston member within said cylinder means, said stop means including a disc-like member having a key-hole type slot formed therein including a central, circular opening and an elongate slot opening to the periphery thereof, and of lesser width than the diameter of said central opening, said piston member including a shaft portion having a diameter receivable in said central opening and a reclosed section adapting said shaft for disposition in the circular opening of said key-hole type slot through said elongate slot opening, said disc-like member being assembled to said cylinder means to limit movement of said piston member and maintain the co-axial orientation thereof with respect to said cylinder means, said cylinder means including a recessed portion in said closed end for retaining a residual supply of air such that said piston member may be disposed in said cylinder means proximate the closed end thereof at atmospheric pressure to trap a quantity of air in said recessed portion, whereby upon evacuation of said vessel a pressure differential will exist across said piston causing said quantity of air to expand and move said piston toward said open end, with the position of said piston member adapted to be employed to provide a visual indication of the existance of a vacuum in said vessel.

4. A medical device according to claim 1 wherein said piston member indicator member comprises a half-disc shaped member arranged to be viewed through a wall of the vessel to provide a visual indication of the position of said piston relative to said cylinder means.

5. A medical device according to claim 1 wherein said piston member head portion includes an annular groove, wherein said O-ring is disposed in said groove and in sliding, sealing engagement with said cylinder walls.

6. A medical device according to claim 1 further including a vial attached to said cover structure interiorly of said vessel, said cylinder means extending into said vial, a label carried by said vial bearing indicia thereon to represent an acceptable and an unacceptable vacuum level, said piston member indicator member extending from said piston member and movable therewith relative to said label to provide a visual indication of the vacuum level in said vessel.

7. A vacuum indicating arrangement for a closed evacuated vessel, said arrangement adapted to be carried by the cover structure or the like of said vessel, said vacuum indicating arrangement including cylinder means having a closed end and an open end, a piston member having a head portion disposed in said open end of the cylinder, an O-ring carried by said head portion in sliding sealed engagement with the interior wall of said cylinder means, a shaft portion extending through said cylinder open end, an indicator member carried by said shaft portion and a guide means at said cylinder open end receiving said shaft to maintain said head portion in co-axial alignment with said cylinder, thereby guiding the sliding sealed movement of said head portion within said cylinder, said cylinder means including a recessed portion in the closed end thereof and said head portion being of lesser diameter dimension than said cylinder to allow said head portion to be inserted into said cylinder open end in a tilted position upon assembly for displacing a quantity of air from said cylinder such that upon disposition of said piston member proximate said closed end a quantity of residual air at atmospheric pressure will remain trapped in said recessed position, such that upon evacuation of said vessel a pressure differential will be created across said piston due to the pressure of said residual quantity of air, which differential will cause said piston to move axially of said cylinder, with the relative position of said piston indicator member in said cylinder employable to provide a visual indication externally of said vessel as to the presence of and the proximate level of vacuum in said vessel.

8. A vacuum indicator arrangement according to claim 7 further including stop means carried by said guide means proximate the open end thereof to retain said piston member within said cylinder means.

9. A vacuum indicator arrangement according to claim 7 wherein said stop means includes a disc-like member having a key-hole type slot formed therein including a central, circular opening and an elongate slot opening to the periphery thereof, and of lesser width than the diameter of said central opening, and said piston member includes a shaft portion having a diameter receivable in said central opening and a reclosed section adapting said shaft for disposition in the circular opening of said key-hole type slot through said elongate slot opening, said disc-like member being assembled to said cylinder means to limit movement of said piston member and maintain the co-axial orientation thereof with respect to said cylinder means.

10. A vacuum indicator arrangement according to claim 7 wherein said piston member indicator member comprises a disc-shaped member arranged to be viewed through a wall of said vessel to provide a visual indication of the position of said piston relative to said cylinder means.

11. A vacuum indicator arrangement according to claim 7 wherein said piston member head portion includes an annular groove, wherein said O-ring is disposed in said groove and in sliding, sealing engagement with said cylinder walls.

* * * * *